United States Patent [19]

Theeuwes

[11] 4,111,201
[45] * Sep. 5, 1978

[54] OSMOTIC SYSTEM FOR DELIVERING SELECTED BENEFICIAL AGENTS HAVING VARYING DEGREES OF SOLUBILITY

[75] Inventor: Felix Theeuwes, Los Altos, Calif.

[73] Assignee: Alza Corporation, Palo Alto, Calif.

[*] Notice: The portion of the term of this patent subsequent to Sep. 5, 1995, has been disclaimed.

[21] Appl. No.: 743,760

[22] Filed: Nov. 22, 1976

[51] Int. Cl.² .................................................. A61M 31/00
[52] U.S. Cl. .................................. 128/260; 206/0.5; 222/130; 222/193; 222/389; 222/395; 222/491; 424/19
[58] Field of Search ............... 128/260, 261, 268, 272; 424/15, 19–22, 33, 37; 222/193, 389, 130, 491, 395; 206/0.5

[56] References Cited

U.S. PATENT DOCUMENTS

| | | | |
|---|---|---|---|
| 3,247,066 | 4/1966 | Milosovich, Jr. | 128/260 |
| 3,732,865 | 5/1973 | Higuchi et al. | 128/260 |
| 3,760,805 | 9/1973 | Higuchi | 128/260 |
| 3,760,984 | 9/1973 | Theeuwes | 128/260 |
| 3,828,777 | 8/1974 | Ness | 128/260 |
| 3,916,899 | 11/1975 | Theeuwes et al. | 128/260 |
| 3,948,254 | 4/1976 | Zaffaroni | 128/260 |
| 3,952,741 | 4/1976 | Baker | 128/260 |
| 3,977,404 | 8/1976 | Theeuwes | 128/260 |
| 3,993,073 | 11/1976 | Zaffaroni | 128/260 |
| 4,008,719 | 2/1977 | Theeuwes et al. | 128/260 |
| 4,014,334 | 3/1977 | Theeuwes et al. | 128/260 |
| 4,016,880 | 4/1977 | Theeuwes et al. | 128/260 |
| 4,036,227 | 7/1977 | Zaffaroni et al. | 128/260 |
| 4,036,228 | 7/1977 | Theeuwes | 128/260 |

*Primary Examiner*—Benjamin R. Padgett
*Assistant Examiner*—T. S Gron
*Attorney, Agent, or Firm*—Paul L. Sabatine; Thomas E. Ciotti; Edward L. Mandell

[57] ABSTRACT

An osmotic system for delivering an agent is disclosed. The system comprises a wall surrounding a compartment and has a passageway through the wall for delivering agent from the compartment. The wall is formed of a material permeable to the passage of an external fluid and impermeable to the passage of agent. The compartment contains an agent that is soluble in the fluid and exhibits an osmotic pressure gradient across the wall against the fluid, or the compartment contains an agent that has limited solubility in the fluid and exhibits a limited osmotic pressure gradient across the wall against the fluid. The compartment also contains a suspending agent and a delivery member for increasing the amount of agent delivered from the system. The delivery member comprises a semipermeable film surrounding an osmotically effective compound and it is able to increase in volume over time. In operation, agent is delivered from the system through the passageway at a controlled rate by fluid being imbibed through the wall into the compartment to produce a solution or suspension containing agent, and for urging the member to increase in volume and fill the compartment, whereby agent is released at a rate controlled by the permeability of the wall, the osmotic pressure gradient across the wall, and the increase in volume of the member over a prolonged period of time.

21 Claims, 11 Drawing Figures

OSMOTIC SYSTEM FOR DELIVERING SELECTED BENEFICIAL AGENTS HAVING VARYING DEGREES OF SOLUBILITY

CROSS-REFERENCE TO RELATED APPLICATION

This application is copending with my U.S. patent application Ser. No. 744,089 filed on Nov. 11, 1976. This application and my copending application are both assigned to the ALZA Corporation of Palo Alto, Calif.

FIELD OF THE INVENTION

This invention pertains to an osmotic system. More particularly, the invention relates to an osmotic system manufactured in the form of an osmotic device comprising an semipermeable wall surrounding a compartment containing an agent, a suspending agent, and a delivery member for increasing the amount of agent delivered from the system over a prolonged period of time.

BACKGROUND OF THE INVENTION

Osmotic systems manufactured in the form of osmotic devices for delivering a beneficial agent to an environment of use are known to the art in U.S. Pat. Nos. 3,845,770 and 3,916,899. The systems disclosed in these patents comprise a semipermeable wall that surrounds a compartment containing an agent. The wall is permeable to an external fluid, substantially impermeable to agent, and there is a passageway through the wall for delivering the agent from the system. These systems release agent by fluid being continuously imbibed through the wall into the compartment at a rate determined by the permeability of the wall and the osmotic pressure gradient across the wall to produce a solution of soluble agent, or a solution of an osmotic attractant containing an agent that has limited solubility in the fluid, which solution in either operation is dispensed from the system. These systems are extraordinarily effective for delivering both an agent that is soluble in the fluid and exhibits an osmotic pressure gradient across the wall against the fluid, and for delivering an agent that has limited solubility in the fluid and is admixed with an osmotically effective compound that is soluble in the fluid and exhibits an osmotic pressure gradient across the wall against the fluid. While the above systems are outstanding and represent a pioneer advancement in the delivery art, and while they are endowed with ideal delivery kinetics useful for delivering numerous beneficial agents at a controlled rate and continuously to environments of use, there is an occasional instance where the delivery kinetics of the system can be unexpectedly improved to lead to more desirable results. For example, the rate of agent delivered by the system is constant for most agents as long as excess solid agent is present in the system with its rate declining parabolically towards zero as the agent's concentration decreases below saturation. That is, both the solubility and the density of the agent influence the amount of agent delivered at a constant rate, and that amount delivered at a declining rate is proportional to the solubility of the agent and inversely proportional to its density. These actions often make it difficult to deliver substantially all of the agent and thereby obtain the full benefit of the agent's specific therapeutic effect, particularly when the agent is very soluble or practically insoluble in the fluid and concomitantly a portion of the agent cannot be delivered at a constant rate over a prolonged period of time. The present invention enhances the amount of these latter agents delivered at a controlled rate and continuously over a prolonged period of time by using a unique combination of a delivery member and a suspending agent to increase the amount of agent delivered from the osmotic system. The osmotic system with the combination also can optionally deliver increased amounts of very soluble or practically insoluble agents as pure agents substantially free of any osmotically effective compounds being mixed therewith. A mathematical presentation pertaining to the instant subject matter is known in *J. Pharm. Sci.*, Vol. 64, No. 12, pages 1987 to 1991, 1975.

OBJECTS OF THE INVENTION

Accordingly, it is an immediate object of this invention to provide an improved osmotic system for the controlled and continuous delivery of an active agent over a prolonged period of time which system overcomes the problems known to the prior art.

Amother object of the invention is to provide an osmotic system that can deliver essentially all of its agent at a controlled and constant rate continuously over a prolonged period of time.

Another object of the invention is to provide an osmotic system for the delivery of a beneficial agent comprising a combination of delivery components that increase the amount of agent delivery from the system.

Yet another object of the invention is to provide an osmotic system having a combination of delivery components for continuously changing the internal volume of the system thereby maintaining the solution or suspension in the system saturated with agent.

Still a further object of the invention is to provide an osmotic system that can maintain the major amount of agent inside the system present as a saturated solution or saturated suspension with excess solid dispersed therein throughout the time agent is released from the system.

Yet stil a further object of the invention is to provide an osmotic therapeutic system that can administer a complete pharmaceutical regimen comprising soluble to very soluble or limited soluble to practically insoluble agents at a constant rate to animals including warm blooded animals and humans for a particular time period, the use of which requires intervention only for initiation and possibly termination of the regimen.

Other objects, features and advantages of the invention will be more apparent to those skilled in the art from the following detailed specification, taken in conjunction with the drawings and the accompanying claims.

SUMMARY OF THE INVENTION

This invention concerns an osmotic system for delivering a beneficial agent to an environment of use. The system comprises a semipermeable wall surrounding a compartment and has a passageway through the wall communicating with the compartment and the exterior of the system. The compartment in a presently preferred embodiment contains an agent that is very soluble in an external fluid and exhibits an osmotic pressure gradient across the wall against the fluid, or in another presently preferred embodiment, it contains an agent having limited solubility in the fluid that exhibits a limited osmotic pressure gradient across the wall against the fluid. The compartment additionally contains a combination of a suspending agent and a delivery member for delivering essentially all of the agent at zero order from the compartment. Optionally, the compartment can contain an osmotically effective compound that exhibits an osmotic pressure gradient across the wall against the fluid as an aid to operate in union with the combination for delivering agent from the system. In operation, agent is released from the system by the combined physico-chemical actions of the system and the combination comprising fluid being imbibed through the wall into the compartment at a rate controlled by the permeability of the wall and the osmotic pressure gradient across the wall to produce a solution or suspension containing suspending agent and beneficial agent and to activate the member to expand in volume, whereby the combined actions cause the system to release beneficial agent at a controlled rate and continuously over a prolonged period of time.

BRIEF DESCRIPTION OF THE DRAWINGS

In the drawings, which are not drawn to scale, but are set forth to illustrate various embodiments of the invention, the figures are as follows.

In the drawings and specification, like parts in related figures are identified by like numbers. The terms appearing earlier in the specification and in the description of the drawings, as well as embodiments thereof, are further detailed elsewhere in the disclosure.

DETAILED DESCRIPTION OF THE DRAWINGS

Figure 1A:
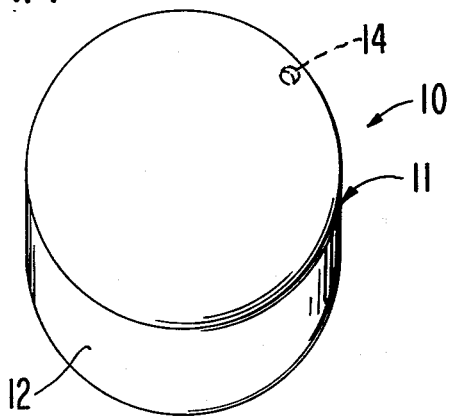
FIG. 1A is a view of an osmotic therapeutic system designed for orally delivering a beneficial agent.
Figure 1B:
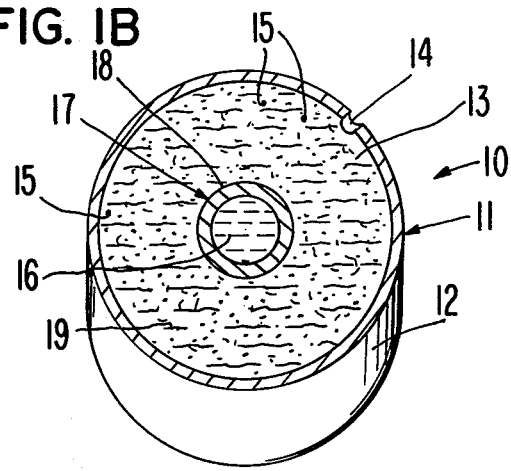
FIG. 1B is a view of the osmotic therapeutic system of FIG. 1A in opened section illustrating the compartment of the system the combination for increasing the amount of the beneficial agent delivered from the system.
Figure 1C:
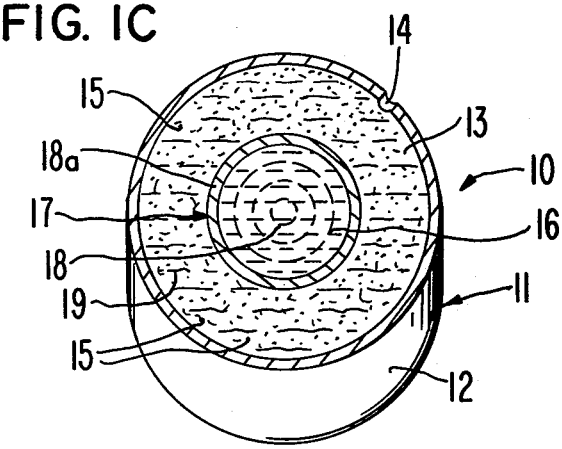
FIG. 1C is a view of the osmotic system of FIG. 1B showing the delivery member in operation as it expands to fill the compartment.

Turning now to the drawings in detail, which are examples of various osmotic delivery systems of the invention, and which examples are not to be considered as limiting, one example of an osmotic delivery system manufactured in the form of an osmotic device is indicated in FIGS. 1A, 1B and 1C, considered together, by the numeral 10. The phrases "osmotic delivery system" and "osmotic delivery system in the form of an osmotic device" as used for the purpose of this invention are used as functional equivalents and they also embrace the expressions "osmotic therapeutic system", "osmotic device", and "system".

In FIGS. 1A, 1B and 1C, system 10 is seen comprised of a body 11 having a wall 12 that surrounds a compartment 13, illustrated in FIGS. 1B and 1C in opened section, and a passageway 14 that communicates with compartment 13 and the exterior of system 10. Compartment 13, as seen in FIG. 1B, in one embodiment contains an agent 15 that is soluble in an external fluid and in a presently preferred embodiment is very soluble in the external fluid and exhibits an osmotic pressure gradient across wall 12 against an external fluid. Compartment 13 is another presently preferred embodiment, contains an agent 15 which has limited solubility or is substantially insoluble in the external fluid and exhibits a limited or it does not exhibit any osmotic pressure gradient across wall 12 against said fluid. In another embodiment, compartment 13 optionally contains a mixture comprising agent 15 which has limited solubility or is substantially insoluble in the field and is mixed with an osmotically effective compound 16 that is soluble in the fluid, and exhibits an osmotic pressure gradient across wall 12 against the fluid, and which compound further aids in delivering agent 13 from system 10.

System 10 also contains in compartment 13 a combination, seen in FIGS. 1B and 1C, for increasing the amount of agent delivered from system 10. The combination comprises: (1) a delivery member 17 formed of a film 18 encapsulating an osmotically effective compound 16, seen in FIG. 1B, that is soluble or swells in fluid imbibed into member 17 from fluid in compartment 13. Film 18 is free of any passageways and it is formed of a material that can move from an initial or rested position, seen in FIG. 1C at 18, through sequential changes as represented by elliptical dotted lins to form member 17 with its film in expanded state 18a. Delivery member 17 of the invention is placed in compartment 13 free of any attachment to wall 12, and member 17 can contain one, or a plurality of osmotically effective compounds 16 with each exhibiting the same or different osmotic pressure gradients across film 18 against the fluid. The combination also comprises (2) a suspending agent illustrated by wavy lines 19. Suspending agent 19 is mixed with beneficial agent 15 and on imbibition of fluid into compartment 13, it forms a suspension containing agent 15. The suspension makes possible the delivery of agent 15 at concentrations greater than its saturation concentration in the fluid. That is, suspending agent 19 and delivery member 17 cooperate and act as a single entity to deliver beneficial agents having limited solubility in the fluid at concentrations higher than their saturation concentrations at a controlled rate and continuously over a prolonged period of time.

Delivery member 17 and suspending agent 19 both operate in cooperation with system 10 to release agent 15 to the environment of use. System 10 releases agent 15 in compartment 13, which agent is soluble or very soluble in the external fluid, or has limited solubility or is practically insoluble in the fluid, by fluid being imbibed into compartment 13, in a tendency toward osmotic equilibrium at a rate controlled by the permeability of wall 12 and the osmotic pressure gradient across wall 12 to continuously dissolve or form a suspension of agent 15 in suspending agent 19 which is osmotically pumped from system 10 through passageway 14 over a prolonged period of time. Delivery member 17 operates to substantially insure that delivery of agent 15 is constant from system 10 by two methods. First, delivery member 17 operates to continuously concentrate agent 15 by imbibing fluid from compartment 13 into delivery member 17 to keep the concentration of agent 15 from falling below saturation; and secondly, delivery member 17 by imbibing fluid continuously expands in size and volume and reduces the volume of compartment 13 thereby correspondingly dispensing agent 15 in solution or suspension from compartment 13. System 10, in another embodiment, releases agent 15 that has limited solubility or is practically insoluble in the fluid and is mixed with an osmotically effective compound, delivery member 17 and suspending agent 19, by fluid being imbibed through wall 12 into compartment 13 in a tendency towards osmotic equilibrium at a rate controlled by the permeability of wall 12 and the osmotic pressure gradient across wall 12 to continuously dissolve the osmotically effective compound and form a solution containing agent in suspension that is pumped from system 10 through passageway 14. In this latter embodiment, delivery component 17 and suspending agent 19 operate as described supra. A detailed mathematical discussion of the operation of member 17 appears later in the specification.

Wall 12 of system 10 is comprised in total or in at least a part of a semipermeable material that is permeable to an external fluid essentially impermeable to agent 15, and ingredients in compartment 13. When wall 12 is formed in part of a semipermeable material, the remainder is formed of an impermeable material. Film 18 of member 17 is formed of a semipermeable material that is deformable and can undergo expansion over a period of time. Wall 12 and film 18 can be formed of synthetic or naturally occurring materials and a detailed description of these materials appears later in the specification.

System 10 of FIGS. 1A, 1B and 1C can be made into many embodiments including the presently preferred embodiments for oral use, that is, for releasing either a locally or systemically acting therapeutic agent in the gastrointestinal tract over a prolonged period of time. Oral system 10 can have various conventional shapes and sizes such as round with a diameter of 3/16 inch to ¼ inch, or it can be shaped like a capsule having a range of sizes from triple zero to zero, and from 1 to 8.

Figure 2A:
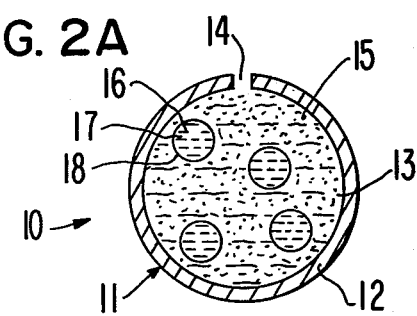
FIG. 2A is another osmotic system in opened section showing the system housing a combination comprising suspending agent and plurality of delivery means.
Figure 2B:
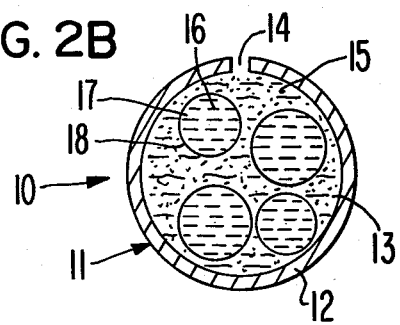
FIG. 2B is a view of FIG. 2A showing the system in operation.

FIGS. 2A and 2B represent another system 10 manufactured according to the invention and designed for administering agent 15 to an environment of use. In FIGS. 2A and 2B, system 10 is seen in opened section and it is similar to system 10 of FIGS. 1A, 1B and 1C, as it comprises a body 11 having a wall 12 that surrounds a compartment 13 having a passageway 14 that communicates with the exterior of system 10. Compartment 13 of system 10 contains a multiplicity of driving members 17 comprising a film 18 encasing an osmotically effective compound 16 and they operate in cooperation with suspending agent 19 as described supra to maintain a concentrated solution or suspension containing excess solid agent 15 for substantially zero order release of agent 15 from system 10 over a prolonged period of time.

Figure 3:
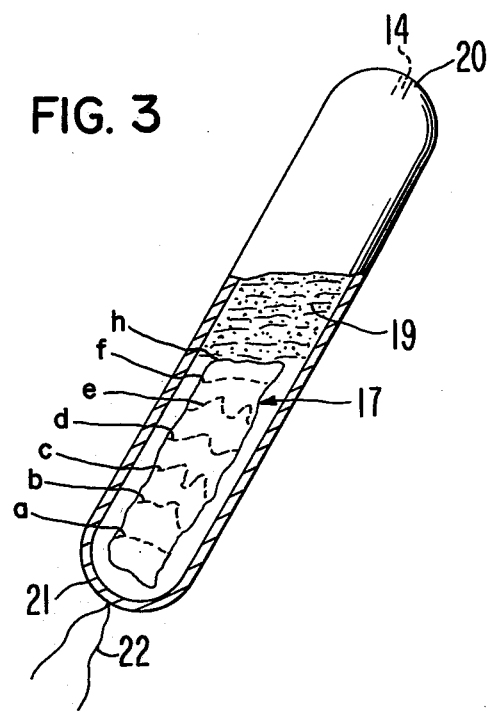
FIG. 3 shows an osmotic therapeutic system designed for releasing drug in the anal cavity of an adult.

FIG. 3 shows an osmotic system 10 designed for placement and release of drug in an anus or other body opening of a warm blooded animal. System 10 has an elongated, cylindrical, self-sustaining shape with a rounded lead end 20, a trailing end 21, and it is equipped with a manually controllable cord 22 for easily removing system 10 from the anus. System 10 is structurally identical with system 10 as described above. System 10 has a delivery member 17 and a suspending agent 19. Member 17 operates by increasing in volume from "$a$" through "$h$", thereby urging a suspension containing drug from system 10 through passageway 14. FIG. 3 in one embodiment contains a drug designed for absorption by the anal mucosa to produce a local or systemic effect.

Figure 4:
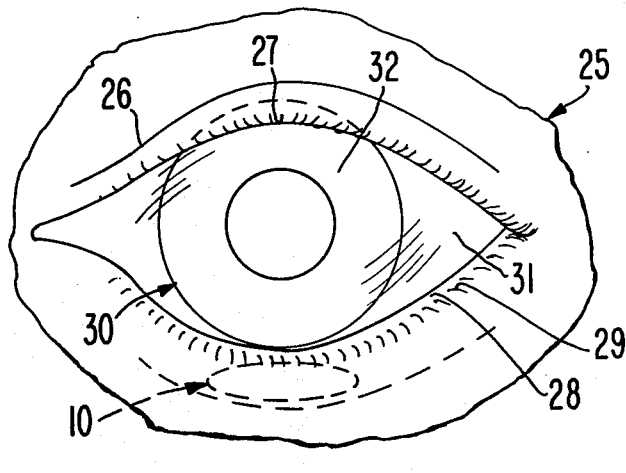
FIG. 4 is a front view of the human eye illustrating an osmotic therapeutic system in operative position to the environment of use.

Referring to FIG. 4, an ocular therapeutic system 10 is seen in an eye 25 for administering drug at an osmotically metered dosage rate thereto. In FIG. 4, eye 25 is comprised of an upper eyelid 26 with eyelashes 27 and lower eyelid 28 with eyelashes 29. Eye 25 anatomically comprises an eyeball 30 covered for the greater part by sclera 31 and at its center area by cornea 32. Eyelids 26 and 28 are lined with an epithelial membrane or palpebral conjunctiva, and sclera 31 is lined with a bulbar conjunctiva that covers the exposed surface of eyeball 30. Cornea 30 is covered with a transparent epithelial membrane. The portion of the palpebral conjunctiva which lines upper eyelid 26 and the underlying portion of the bulbar conjunctiva defines an upper cul-de-sac, while that portion of the palpebral conjunctiva which lines lower eyelid 28 and the underlying portion of the bulbar conjunctiva defines a lower cul-de-sac. Ocular osmotic system 10, seen in broken lines, is designed for placement in the upper or lower cul-de-sac. System 10 is seen in the lower cul-de-sac and it it held in place by the natural pressure of lower eyelid 28. System 10 contains an ophthalmic drug for release to eye 25 at a controlled rate and continuously over a prolonged period of time.

Ocular system 10 can have any geometric shape that fits comfortably in the eye or in the cul-de-sac. Typical shapes include, ellipsoid, bean, banana, circular, ring, rectangular, square, doughnut, crescent and half-ring shaped systems. In cross-section, the systems can be doubly convex, concavo-convex, rectangular and the like, as the device in use will tend to conform to the shape of the eye. The dimensions of an ocular system can vary widely with the lower limit governed by the amount of drug to be administered to the eye as well as the smallest sized system that can be placed and positioned in the eye. The upper limit on the size of the system is governed by the space limitation in the eye consistent with comfortable retention in the eye. Satisfactory systems have a length of 4 to 20 millimeters, a width of 1 to 15 millimeters. The ocular system can contain from 0.15 micrograms to 100 milligrams of drug, or more, and it is made from materials non-toxic to the eye.

While FIGS. 1 through 4 are illustrative of various osmotic delivery systems that can be made according to the invention, it is to be understood these systems are not to be construed as limited, as the system can take a wide variety of shapes, sizes and forms for delivering agent to different environments of use. For example, the system includes buccal, implant, vaginal, artificial gland, cervical, intrauterine, ear, nose, dermal, subcutaneous, and blool delivery systems. The systems also can be adapted for delivering an active agent in streams, aquariums, fields, factories, reservoirs, laboratory facilities, hot houses, transportation means, naval means, military means, hospitals, veterinary clinics, nursing homes, farms, zoos, chemical reactions, and other environments of use.

DETAILED DESCRIPTION OF THE INVENTION

In accordance with the practice of the invention, it has now been found that osmotic delivery system 10 can be manufactured with a wall 12 formed of a material that does not adversely affect the agent, an animal, or other host, and is permeable to an external fluid such as water and biological fluids while essentially impermeable to agents, drugs and the like. The selectively permeable materials forming wall 12 are insoluble in body fluids, and they are non-erodible, or they can be bioerodible after a predetermined period with bioerosion corresponding to the end of the agent release period. Typical materials for forming wall 12 include materials known to the art as semipermeable membranes including osmosis and reverse osmosis membranes such as cellulose acetate, cellulose triacetate, agar acetate, amylose triacetate, beta glucan acetate, cellulose diacetate, acetaldehyde dimethyl acetate, cellulose acetate ethyl carbamate, polyamides, polyurethane, sulfonated polystyrenes, cellulose acetate phthalate, cellulose acetate methyl carbamate, cellulose acetate succinate, cellulose acetate dimethylaminoacetate, cellulose acetate ethyl carbamate, cellulose acetate chloroacetate, cellulose dipalmitate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, selectively permeable polymers formed by the coprecipitation of a polycation and a polyanion as disclosed in U.S. Pat. Nos. 3,173,876; 3,276,586; 3,541,005; 3,541,006; and 3,546,142. Generally, semipermeable materials useful for forming wall 12 will have a fluid permeability of $10^{-5}$ to $10^{-1}$ (cc mil/cm$^2$ hr atm) expressed per atmosphere of hydrostatic or osmotic pressure difference across wall 12 at the temperature of use. Suitable materials are known to the art in U.S. Pat. Nos. 3,845,770 and 3,916,899.

Film 18 of member 17 is formed of the above materials and it additionally contains from 0.01 to 40% of a film expansion agent that imparts flexibility, deformability and expansion properties to the film. Suitable agents in one embodiment include polyhydric alcohols and derivatives thereof, such as polyalkylene glycols of the formula H-(O-alkylene)$_n$—OH wherein the bivalent alkylene radical is straight or branched chain and has from 1 to 10 carbon atoms and $n$ is 1 to 500 or higher. Typical glycols include polyethylene glycols 300, 400, 600, 1500, 1540, 4000 and 6000 of the formula H—(OCH$_2$CH$_2$)$_n$—OH wherein $n$ is respectively 5, 5.7, 8.2 to 9.1, 12.5 to 13.9, 29 to 36, 29.8 to 37, 68 to 84, and 158 to 204. Other polyglycols include low molecular weight glycols such as polypropylene, polybutylene and polyamylene.

The film expansion agents in another embodiment include poly($\alpha,\omega$)-alkylenediols wherein the alkylene is straight or branched chain of from 2 to 10 carbon atoms such as poly(1,3)-propanediol, poly(1,4)-butanediol, poly(1,5)-pentanediol and poly(1,6)-hexanediol. The diols also include aliphatic diols of the formula HOC$_n$H$_{2n}$OH wherein $n$ is from 2 to 10 and the diols are optionally bonded to a non-terminal carbon atom such as 1,3-butylene glycol, 1,4-pentamethylene glycol, 1,5-hexamethylene glycol and 1,8-decamethylene glycol; and alkylenetriols having 3 to 6 carbons atoms such as glycerine, 1,2,3-butanetriol, 1,2,3-pentanetriol, 1,2,4-hexanetriol and 1,3,6-hexanetriol.

Other film expansion agents include esters and polyesters of alkylene glycols of the formula HO—(alkylene-O)$_n$—H wherein the divalent alkylene radical includes the straight chain groups and the isomeric forms thereof having from 2 to 6 carbons and $n$ is 1 to 14. The esters and polyesters are formed by reacting the glycol with either a monobasic or dibasic acid. Exemplary agents are ethylene glycol dipropionate, ethylene glycol butyrate, ethylene glycol diacetate, triethylene glycol diacetate, butylene glycol dipropionate, polyester of ethylene glycol with succinic acid, polyester of diethylene glycol with maleic acid and polyester of triethylene glycol with adipic acid.

Exemplary film expansion agents suitable for the present purpose generically include agents that lower the temperature of the second-order phase transition or the glass transition temperature of the film forming materials or the elastic modulus thereof, increase the workability of the film, its flexibility, and its permeability to fluid. Agents operable for the present purpose include both cyclic and acyclic agents. Typical agents are those selected from the group consisting of phthalates, phosphates, citrates, adipates, tartrates, sebacates, succinates, glycolates, glycerolate, benzoates, myristates, sulfonamides, and halogenated phenyls.

Exemplary film expansion agents further include dialkyl phthalates, dicycloalkyl phthalates, diaryl phthalates and mixed alkyl-aryl phthalates as represented by dimethyl phthalate, dipropyl phthalate, di(2-ethylhexyl)-phthalate, di-isopropyl phthalate, diamyl phthalate and dicapryl phthalate; alkyl and aryl phosphates such as tributyl phosphate, trioctyl phosphate, tricresyl phosphate, trioctyl phosphate, tricresyl phosphate and triphenyl phosphate; alkyl citrate and citrate esters such as tributyl citrate, triethyl citrate, and acetyl triethyl citrate; alkyl adipates such as dioctyl adipate, diethyl adipate and di(2-methoxyethyl)-adipate; dialkyl tartrates such as diethyl tartrate and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycerolates, glycol esters and glycerol esters such as glycerol diacetate, glycerol triacetate, glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate. Also, camphor, N-ethyl-(o- and p-toluene) sulfonamide, chlorinated biphenyl, benzophenone, N-cyclohexyl-p-toluene sulfonamide, and substituted epoxides.

Suitable film expansion agents can be selected for blending with the film forming materials by selecting agents that have a high degree of solvent power for the materials, are compatible with the materials over both the processing and use temperature range, exhibit permanence as seen by a strong tendency to remain in the film, impart the desired properties, and are non-toxic to animals, humans, avians, fishes and reptiles when the osmotic system is used for dispensing drugs. Procedures for selecting an agent having the described characteristics are disclosed in the *Encyclopedia of Polymer Science and Technology,* Vol. 10, pages 228 to 306, 1969, published by John Wiley & Sons, Inc.

The expression "passageway" as used herein comprises means and methods suitable for releasing the agent from the system. The expression includes aperture, orifice or bore through wall 12 formed by mechanical procedures, or by eroding an erodible element, such as a gelatin plug, in the environment of use. Generally, the passageway will have an opening of 4 to 40 mils or larger; and it will be large enough to permit passage of the suspended particles. A detailed description of osmotic passageways and the maximum and minimum dimensions for a passageway are disclosed in U.S. Pat. Nos. 3,845,770 and 3,916,899. These patents are assigned to the Alza Corporation of Palo Alto, Cal., the assignee of this application.

The osmotically effective compounds that can be used for the purpose of the invention include inorganic and organic compounds that exhibit an osmotic pressure gradient against an external fluid across wall 12 and across film 18. These compounds are known as osmagents. The osmagents when present in compartment 13 are mixed with an agent that has limited solubility in external fluid with the osmagent forming a saturated solution containing agent that is osmotically delivered from the system. The osmagents are present in member 17 for: (a) imbibing fluid from compartment 13 to concentrate a solution or a suspension in compartment 13; and (b) for member 17 to expand and fill the volume of compartment 13. the osmagents are used in compartment 13 by homogenously or heterogenously mixing it or a mixture of osmagents with an agent, either before they are charged into the compartment, or by self-mixing after they are charged into the compartment. In operation, these osmagents attract fluid into the compartment producing a solution or suspension of osmagents and suspending agent which is delivered from the system concomitantly transporting undissolved and dissolved agent to the exterior of the system. The osmagents are present in the member 17 independent of the presence of any other agent. Osmotically effective compounds, or osmagents useful for the present purpose in 13 and 17 include salts such as magnesium sulfate, magnesium chloride, sodium chloride, lithium chloride, potassium sulfate, sodium carbonate, sodium sulfate, lithium sulfate, potassium chloride, ammonium chloride, calcium carbonate, sodium sulfate, calcium sulfate, potassium acid phosphate, calcium lactate, mannitol, urea, inositol, magnesium succinate, tartaric acid, carbohydrates such as raffinose, sorbitol, succrose, fructose, glycose, and mixtures thereof. The osmagent suitable for housing in member 17 also includes algin, sodium alginate, potassium alginate, carrageenan, fucoridan, furcellaran, laminaran, hypnea, pectin, and the like. The osmagent is usually present in an excess amount, and it can be in any physical form such as particle, crystal, pellet, tablet, strip, powder, film or granule. The osmotic pressure $\pi$, in atmospheres ATM, of the osmagents suitable for the invention will be greater than zero ATM, generally from zero ATM up to 500 ATM, or higher.

The expression "active agent" as used herein broadly includes any compound, composition of matter or mixture thereof, that can be delivered from the system to produce a beneficial and useful result. The beneficial agent can be soluble in a fluid that enters the compartment and functions as its own osmotically effective solute, and is mixed with a suspending agent, or it can have limited solubility in the fluid and be mixed with a suspending agent; and optionally in the latter embodiment, it can be mixed with an osmotically effective compound soluble in fluid that is delivered from the system. The active agent includes pesticides, herbicides, germicides, biocides, algicides, rodenticides, fungicides, insecticides, anti-oxidants, plant growth promoters, plant growth inhibitors, preservatives, anti-preservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, micro-organism attenuators, and other agents that benefit the environment of use.

In the specification and the accompanying claims, the term "drug" includes any physiologically or pharmacologically active substance that produces a localized or systemic effect or effects in animals, including warm blooded animals, mammals, humans, primates, avians, domestic household animals, sport and farm animals such as sheep, goats, cattle, horses and pigs, for administering to laboratory animals such as mice, rats and guinea pigs, and to fishes, reptiles, jungle and zoo animals. The active drug that can be delivered includes inorganic and organic compounds without limitation, those materials that act on the central nervous system such as hypnotics and sedatives, psychic energizers, tranquilizers, antidepressants, anticonvulsants, muscle relaxants, antiparkinson agents, analgesics, anti-inflammatory, local anesthetics, muscle contractants, anti-infectives, anti-microbials, anti-malarials, hormonal agents, sympathomimetics, metabolic aberration correcting agents, diuretics, anti-parasitics, neoplastics, hypoglycemics, nutritionals, fats, ophthalmic, electrolytes, cardiacs, and diagnostic agents.

Exemplary of drugs that are very soluble in water and can be delivered by the systems of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproternol sulfate, methamphetamine hydrochloride, phenmetrazine hydrochloride, bethanechol chloride, methacholine chloride, pilocarpine hydrochloride, atropine sulfate, methscopolamine bromide, isopropamide iodide, tridihexethyl chloride, phenformin hydrochloride, and methylphenidate hydrochloride.

Exemplary of agents that are very slightly soluble or practically insoluble in water that can be delivered by the system of this invention include diphenidol, meclizine hydrochloride, prochlorperazine maleate, thiethylperazine maleate, anisindione, diphenadione, erythrityl tetranitrate, dizoxin, isoflurophate, reserpine, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, steroids, including corticosteroids such as hydrocortisone, desoxycorticosterone acetate, cortisone acetate, triamcinolone, androgens such as methyltesterone, estrogenic steroids such as 17$\beta$-estradiol, and ethinyl estradiol, and progestational steroids such as 17$\alpha$-hydroxyprogesterone acetate, 19-nor-progesterone, prednisolone, norethindrone acetate, progesterone, norethynodrel, and the like.

The drug also can be in various forms, such as uncharged molecules, molecular complexes, pharmacologically acceptable acid or base addition salts such as hydrochlorides, hydrobromides, sulfate, laurylate, palmitate, phosphate, nitrate, borate, acetate, maleate, tartrate, oleate, and salicylate. For acidic drugs, salts of metals, amines or organic cations, for example quaternary ammonium can be used. Derivatives of drugs such as esters, ethers and amides can be used alone or mixed with other drugs. Also, a drug that is water insoluble can be used in a form that on its release from the device, is converted by enzymes, hydrolyzed by body pH or other metabolic processes to the original form, or to a biologically active form. The agent can be in the reservoir as a dispersion, paste, cream, particle, granule, emulsion, suspension or powder. Also, the agent can be mixed with a binder, diluent, dispersant, stabilizer, emulsifier or wetting agent and dyes.

The amount of agent present in the system is initially in excess of the amount that can be dissolved in, mixed, or suspended with the fluid that enters the compartment and the suspending agent. Under this physical state when the agent is soluble and in excess, or if the agent is mixed with an osmagent, the system will osmotically operate to give a substantially constant rate of release. The rate of agent release pattern can also be varied by having different amounts of agent in the compartment to form solutions, suspensions or mixtures containing different concentrations of agent, and optionally, osmagents for delivery of agents from the system. Generally, the system can house from 0.05 ng to 5 grams or more of agent, with individual systems containing for example, 25 ng, 1 mg, 5 mg, 250 mg, 500 mg, 1.5 g, of agent or mixtures thereof, and the like. The beneficial drugs are known to the art in *Pharmaceutical Sciences*, by Remington, 15th Ed., 1975, published by Mack Publishing Co., Easton, Penna; *The Drug, The Nurse, The Patient, Including Current Drug Handbook*, 1974–1976, by Falconer, et al., published by Saunder Company, Philadephia, Penna; and, *Medicinal Chemistry*, 3rd Ed., Vol. I & II, by Burger, A., published by Wiley-Interscience, New York.

The solubility or insolubility of an agent in an external fluid can be determined by various art known techniques. One method consists in preparing a saturated solution or suspension comprising the external fluid plus the agent and ascertaining by analyzing the amount of agent present in a definite quantity of the fluid. A simple apparatus for this purpose consists of a test tube of medium size fastened upright in a water bath maintained at constant temperature and pressure in which the fluid and agent are placed and stirred by a motor driven rotating glass spiral. After a given period of stirring, a definite weight of the fluid is analyzed and the stirring continued for an additional period of time. If the analysis shows no increase of dissolved or suspended agent after successive periods of stirrings, in the presence of excess solid agent in the fluid, the solution or suspension is saturated and the results are taken as the solubility of the product in the fluid. Optionally, if the agent is soluble an osmagent is not needed; if the agent has limited solubility or if it is insoluble in the fluid, then an osmagent can optionally be incorporated into the compartment already housing the delivery component. Numerous other methods are available for determining the solubility of an agent in a fluid. Typical methods used for measuring solubility include chemical analysis, ultra violet spectrometry, density, refractive index and electrical conductivity. Generally, for the purpose of this invention soluble to very soluble agents will dissolve in the range of from 175 mg to 900 mg of agent or higher per milliter of fluid, and limited soluble to insoluble agents will dissolve in the range of 0.001 mg to 125 mg of agent per milliter of fluid. While the invention has been described with particular reference to presently preferred embodiments including soluble and insoluble, it is understood the system of the invention can be used to deliver other agents having other degrees of solubilities. Details of various methods for determining solubilities are described in *United States Public Health Service Bulletin*, No. 67 of the Hygienic Laboratory; *Encyclopedia of Science and Technology*, Vol. 12; pages 542 to 556, 1971, published by McGraw-Hill, Inc.; and *Encyclopaedic Dictionary of Physics*, Vol. 6, pages 547 to 557, 1962, published by Pergamon Press, Inc.

Suspending agents suitable for the purpose of this invention are those materials that can form a suspension containing the beneficial agent. For the present purpose, a suspension is a dispersion containing a divided or a finely divided agent having limited solubility, or is insoluble in fluid entering the compartment. The agent is suspended in a liquid suspending medium, which physical state is initially present, or is formed in the compartment. The particles have an effective particle size able to form a suspension and for osmotic release from the system. Generally, the effective particle size is in the range of 0.01 to 300 microns. The particles can be made by first grinding the agent in a ball mill, and then in a colloid mill. The effective particle size can be measured with a Coulter counter.

Suspending agents suitable for the present purpose include hydrophilic suspending agent, anionic fluid soluble suspending compounds, and agents such as carboxymethyl cellulose, gelatin, pectin, polyvinyl pyrrolidone, polyethylene glycol 6000, polypropylene glycol 1200, hydroxyethyl cellulose, alkoxystarches, ethoxystarch, polyoxyalkylene glycols and their ethers, and the like. Generally, the suspending agents will exhibit very little osmotic pressure gradient across the wall and they are present from 1 to 50% by weight, of the total weight of all constituents housed in the compartment.

The systems of the invention are manufactured by standard techniques. For example, in one embodiment, the agent, the delivery component, and other ingredients that may be housed in the compartment and a solvent are mixed into a solid, semi-solid or gel by conventional methods such as ballmilling, calendering stirring or rollmilling and then pressed into a preselected shape. The wall forming the system can be applied by molding, spraying or dipping the pressed shape into wall forming materials. In another embodiment, a wall can be cast, shaped to the desired dimensions to define a wall that surrounds a compartment that is filled with agent and means, and then closed. The system also can be manufactured with an empty compartment that is filled through the passageway. Walls forming the system also can be joined by various joining techniques such as high frequency electronic sealing that provides clean edges and firmly formed walls. Another, and presently preferred technique that can be used is the air suspension procedure. This procedure consists in suspending and tumbling the agent and means in a current of air and a wall forming composition until the wall is applied to the agent. The means comprising the film surrounding the osmagent can be manufactured by the above techniques. Also, the air suspension procedure is well-suited for independently forming the means by applying a film to an osmagent. The air suspension procedure is described in U.S. Pat. No. 2,799,241; in *J. Am. Pharm. Assoc.*, Vol. 48, pages 451 to 459, 1959; and ibid., Vol. 49, pages 82 to 84, 1960. Other wall forming and film forming techniques such as pan coating can be used in which the materials are deposited by successive spraying of the polymer solution on the agent or osmagent tumbling in a rotating pan. Other standard manufacturing procedures are described in *Modern Plastics Encyclo-*

*pedia*, Vol. 46, pages 62 to 70, 1969; and in *Pharmaceutical Sciences*, by Remington, 14th Ed., pages 1626 to 1678, 1970, published by Mack Publishing Company, Easton, Penna.

Exemplary solvents suitable for manufacturing the wall, or the film include inert inorganic and organic solvents that do not adversely harm the wall forming materials, the film forming materials, and the final system. The solvents broadly include members selected from the group consisting of aqueous solvents, and organic solvents, such as alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol.

DESCRIPTION OF EXAMPLES OF THE INVENTION

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

An osmotic delivery device for the controlled and continuous release of a beneficial agent to an environment of use is constructed as follows: first, a delivery member is formed by encapsulating a given amount of an osmagent with a film consisting of a semipermeable material and a film expansion agent in an air suspension machine. Next, the member is mixed and compressed with a water soluble beneficial agent 15 that can exhibit an osmotic pressure gradient across a wall and a suspending agent 19 and then they are surrounded with a semipermeable polymeric wall forming material. A passageway is drilled in the wall to form a system having a compartment housing both agents and the delivery member.

Figure 5:
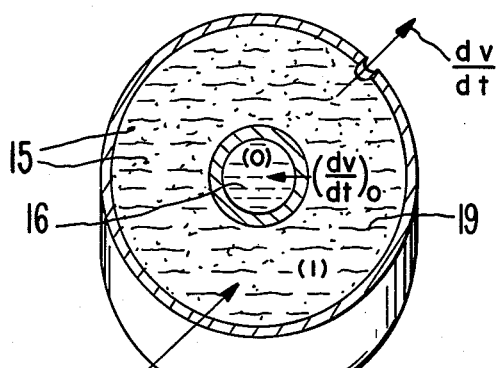
FIG. 5 shows an opened osmotic delivery system illustrating the cooperative relationship between the parts of the system.

The system of this example is illustrated in FIG. 5, and it releases agent at a zero order rate over a prolonged period of time. In FIG. 5 the beneficial agent compartment is identified by (1), the delivery member is identified as (0), the suspending agent by wavy lines 19, and the delivery from the system 10 is governed by the osmotic pressure of the active agent 15 at the volume flow rate $(dv/dt)_1$ as given by Relation 1:

$$[dv/dt]_1 = K_1 \cdot (A_1/h_1) \cdot \pi_{1s} \quad (1)$$

wherein $K$ is the fluid (water in this example) permeability of the wall of the system, $\pi_{1s}$ is the osmotic pressure of the agent at saturation, $A_1$ is the area of the wall, and $h_1$ is the thickness of the wall, and the mass zero order delivery rate is given by Relation 2:

$$dm_{1s}/dt = [dv/dt]_1 \cdot C_{1s} \quad (2)$$

wherein $C_{1s}$ is the concentration of agent 15 at saturation. The volume flow rate from the system $dv/dt$ is given by Relation 3, indicating that the volume flow rate from the system is equal to the volume of liquid imbiled into compartment (1):

$$[dv/dt] = [dv/dt]_1 \quad (3)$$

It is practical to assume $\pi_0$ is equal to a constant, or that sufficient osmagent is available in the means. The effective osmotic pressure of the osmagent in the means can be selected as shown by Relation 4:

$$\pi_0 \leq \pi_{1s} \quad (4)$$

such that delivery promoted by the member is temporarily delayed until all solid agent 15 in the compartment is delivered from the system. When all of agent 15 is delivered, the member starts to imbibe water from the compartment at a rate $(dv/dt)_0$ which is equal to the volume change $dv_0/dt$ of the member and also equal to the volume change of the compartment $dv_1/dt$. The total volume flow from the system is given by Relation 5:

$$\frac{dv}{dt} = \underbrace{\left[\frac{dv}{dt}\right]_1 - \left[\frac{dv}{dt}\right]_0 + \frac{dv_1}{dt}}_{= 0} \quad (5)$$

The volume flow terms in Relation 5 can be expressed as they relate to their individual wall and film permeabilities, and dimensions as given by Relations 6, 7 and 8:

$$\left[\frac{dv}{dt}\right]_1 = k_1 \pi_1 \frac{A_1}{h_1} \quad (6)$$

$$\frac{dv_0}{dt} = \left[\frac{dv}{dt}\right]_0 = k_0 \cdot \frac{A_0}{h_0} [(\pi_0 - \pi_1) - \Delta P] \quad (7)$$

$$\frac{dv_0}{dt} = \frac{-dv_1}{dt} \quad (8)$$

By selecting films having sufficient flexible or expansion properties for the member, $\Delta P$ in Relation 7 can be neglected. The mass of agent is solution in the compartment after all excess solid is delivered is given by Relation 9:

$$m_1 = c_1 v_1 \quad (9)$$

wherein $m_1$ is the mass of agent in solution in the compartment, $c_1$ is the concentration of agent in solution and $v_1$ is the volume of the compartment. The mass changes in the compartment are related to volume and concentration as set forth in Relation 10:

$$\frac{dm_1}{dt} = c_1 \frac{dv_1}{dt} + v_1 \frac{dc_1}{dt} \quad (10)$$

with the mass change $dm_1/dt$ given by Relation 11 as related to the systems delivery rate:

$$-\frac{dm_1}{dt} = c_1 k_1 \pi_1 \frac{A_1}{h_1} \qquad (11)$$

By substituting Relation 11 and Relation 7 into Relation 10, the general differential equation evolves as set forth in Relation 12:

$$-c_1 k_1 \pi_1 \frac{A_1}{h_1} = v_1 \frac{dc_1}{dt} - c_1 k_0 \frac{A_0}{h_0}(\pi_0 - \pi_1) \qquad (12)$$

The differential Relation 11 can be solved to obtain $c_1$ as a function of time, and also to give the delivery rate from the system as a function of time. After the initial zero order delivery rate is obtained from the system as described by Relation 2, a second zero order state can be programmed during which the concentration change in the compartment is zero as shown by Relation 13:

$$dc_1/dt = 0 \qquad (13)$$

The equilibrium osmotic pressure $\pi_1$ which develops in the compartment under this condition is obtained from Relation 12 and 13 and gives Relation 14:

$$\pi_1 = \left[\frac{\pi_0}{1 + \frac{k_1 A_1/h_1}{k_0 A_0/h_0}}\right] \qquad (14)$$

With the new or second zero order steady state concentration $c_1$ can be calculated by Van' Hoff Law according to Relation 15:

$$\pi_1/\pi_{1s} = C_1/C_{1s} \qquad (15)$$

The new second zero order rate is expressed by Relation 16 which is analagous to Relation 11, wherein $\pi_1$ is given by Relation 14, and $c_1$ is given by Relation 15:

$$\frac{dm_1}{dt} = k_1 \frac{A_1}{h_1} \cdot \frac{\pi_0^2}{\left[1 + \frac{k_1 A_1/h_1}{k_0 A_0/h_0}\right]^2} \cdot \frac{C_{1s}}{\pi_{1s}} \qquad (16)$$

This new steady state expressed by Relation 16 can be selected to be equal to the initial agent delivery rate expressed by Relation 2 if the means has the same osmotic pressure as the agent as expressed by Relation 17 when the conditions of Relation 18 hold.

$$\pi_0 = \pi_1 s \qquad (17)$$

$$k_0(A_0/h_0) >> k_1(A_1/h_1) \qquad (18)$$

Conditions 17 and 18 are then sufficient criteria to arrive at a zero order rate from the system for the total lifetime of the device if sufficient driving agent is included to keep $\pi_0$ substantially constant. The minimum mass of driving member $M_0$ needed to sustain zero order is obtained from the driving agent's solubility, $S_0$, in mass per unit volume solution and the system total inside volume $V_{10} + V_{00}$ is given by Relation 19:

$$M_0 \gtrsim S_0(V_{10} + V_{00}) \qquad (19)$$

wherein $V_{10}$ and $V_{00}$ are the initial agent and driving agent volumes, and for a driving agent with a density $\rho_0$, Relation 20 holds as follows:

$$\rho_0 V_{00} \gtrsim S_0(V_{10} + V_{00}) \qquad (20)$$

and for convenience is expressed as Relation 21:

$$\frac{V_{00}}{V_{10}} \gtrsim \left[\frac{1}{\frac{\rho_0}{S_0} - 1}\right] \qquad (21)$$

for all agents 15 and driving membranes of the same density $M_0/M_{01} = V_0/V_{01}$. The above discussion is illustrated in FIG. 5 which shows the relationship between the volume of fluid being imbibed into the compartment in unit time expressed as $(dv/dt)_n$, the volume of fluid being imbibed into the member in unit time expressed as $(dv/dt)_0$ and the volume of fluid leaving the system in unit time $dv/dt$.

EXAMPLE 2

The procedure employed in this example uses the relations of Example 1. In this example it is assumed the osmotic pressure generated by the osmagent in the member is substantially equal to the osmotic pressure generated by agent 15 in the compartment, and that the permeability of the film encapsulating the member is substantially equal to the permeability of the wall of the system $k_0 \simeq k_1$. The use of the expansion agent in the film allows it to stretch such that back pressure is small compared to the osmotic pressure of the osmagent and the member therefore will increase in volume at a constant rate according to Relation 22:

$$A_0/h_0 >> A_1/h_1 \qquad (22)$$

wherein $A_0$ is the area of the member, $h_0$ is the thickness of the film of the member, $A_1$ is the area of the system and $h_1$ is the thickness of the wall of the system.

For a system of size $A \simeq 3$ cm$^3$ and $h_1 \simeq 10$ mils then the ratio of $A_1$ to $h_1$ is given by Relation 23:

$$A_1/h_1 \simeq 4.6 \times 10^4 \text{ mils} \qquad (23)$$

and for a member having a spherical shape and a radius $r_0$, and a film thickness $h_0$, the ratio of $A_0$ to $h_0$ is given by Relation 24:

$$\frac{A_0}{h_0} = n \times \frac{4 \times \pi \times r_0^2}{h_0} \qquad (24)$$

wherein $n$ is the number of members in the compartment. Relation 24 also can be expressed as Relation 25:

$$\frac{A_0}{h_0} = 4 \times \pi \left[\frac{r_0}{h_0}\right]^2 \times h_0 \times n \qquad (25)$$

and for an area to thickness ratio selecting $r_0/h_0$ equal to 10, and for a film thickness of $h_0$ equal to 1 mil, Relation 26 holds as follows:

$$A_0/h_0 = n \times 1.2 \times 10^3 \text{ mil} \qquad (26)$$

with the number of members needed to satisfy Relation 22, taking $A_0/h_0$ as a factor 100 times larger, is then obtained from Relations 23 and 26 and now expressed by Relation 27:

$$n = 4 \times 10^3 \quad (27)$$

The weight of 4,000 means with a radius $r_0$ equal to 10 mil with a density $\rho_0$ equal 1 g/cm$^3$ is expressed by Relation 28:

$$M_0 = (4/3) \pi [r_0]^3 \times n \times \rho_0 \text{ gram} \quad (28)$$

resulting in Relation 29:

$$M_0 = 65 \,\mu\text{g} \times n = 260 \text{ mg} \quad (29)$$

Thus, to keep a constant driving action with this mass of means $M_0$ as expressed by Relation 29, $M_0$ must be larger than $M_0$ expressed by Relation 19, and for a system containing 500 mg of agent, 260 mg of means is required to satisfy Relation 21 if the solubility of the osmagent $S_0$ does not exceed 650 mg/ml.

EXAMPLE 3

Repeating the relations of Examples 1 and 2, and using an osmagent having a solubility $S_{01}$, the minimum amount of osmagent, mass $M_0$, can be calculated from Relation 19 for delivering an amount of agent $M_{01}$, with $M_0$ having a radius $r_0$, the amount is obtained from Relation 28 expressed as Relation 30:

$$r_0^3 = \frac{3}{4\pi} \times \frac{M_0}{\rho_0} \times \frac{1}{n} \quad (30)$$

The quantities $r_0$ and $n$ are further defined by Relation 22, quantitively expressed by Relation 31 in which F expresses the closeness of the second zero order rate to first zero order rate:

$$4 \times \pi \times r_0^2 \times \frac{n}{h_0} = F\left[\frac{A_1}{h_1}\right] \quad (31)$$

with $r_0$ and $n$ two viables which simultaneously have to satisfy Relations 30 and 31 as given by Relations 32 and 33:

$$r_0 = \frac{3 M_0}{h_0 \pi_0} \frac{1}{F(A_1/h_1)} \quad (32)$$

$$n = 8.8 \times 10^{-3} \frac{F^3 (A_1/h_1)^3 h_0^3}{(M_0/\rho_0)^2} \quad (33)$$

The above presentation demonstrates that film encapsulating osmagents functioning in the presence of a suspending agent substantially increases the zero order delivery rate of a given osmotic system even when F equals 10, which would in Example 2 correspond to a driving mass $M_0$ equal to 26 mg for a final zero rate being 90% of the original zero order rate.

EXAMPLE 4

An oral osmotic therapeutic system for administering water insoluble drugs is manufactured having the structure shown in FIG. 5. Member (0) is the driving force and it contains an osmagent surrounded with an expandable membrane. Compartment (1) contains an insoluble drug dispersed and suspended in a viscous water permeable medium. The viscous medium can be a solid at room temperature and liquid at body temperature, or a liquid created in situ comprises a powder such as gelatin mixed with a salt or sugar and the drug. During the start-up time, the sugar or salt will cause water to be imbibed to create a suspension. The sugar or salt will be first pumped out of the compartment, at which time the driving member will assume the driving function. The volume drug delivery rate is then equal to the swelling rate or increase in volume of member (0).

The flux of water into member (0) is governed by the osmotic pressure $\pi_0$, and the composite membrane of member (0), and the membrane of the compartment (1). The swelling rate and drug volume delivery rate is given by the Relation: 34:

$$\frac{dv}{dt} = \pi_0 \frac{1}{\frac{h_0}{A_0 k_0} + \frac{h_1}{A_0 k_0}} \quad (34)$$

wherein $h$, $k$ and A have the meanings given above, the symbol (0) is used to describe driving member (0). A constant rate is obtained for the relation which is expressed by Relations 35 and 36:

$$\frac{h_0}{A_0 k_0} << \frac{h_1}{A_1 k_1} \quad (35)$$

$$\frac{A_0 k_o}{h_0} >> \frac{A_1 k_1}{h_1} \quad (36)$$

Constant controlled delivery is obtained, in this situation since $A_1$, $k$ and $h_1$ are constant throughout the lifetime of the device.

When $h_0/A_0 k_0$ is selected to be important compared to $h_1/A_1 k_1$ the delivery rate can be programmed to increase as a function of time since $h_1/A_1$ is a decreasing function for swelling particles.

Relation 35 is equal to Relation 15 obtained through Relation 19 and in both cases for delivery of soluble and insoluble drugs it is of interest to construct fast swelling particles of high surface to membrane thickness ratio. The amount, $M_0$, of driving agent to be included in order to keep a constant rate is again given by Relation 16.

EXAMPLE 5

An osmotic therapeutic system manufactured in the form of an oral, osmotic device for delivering procainamide hydrochloride to the gastrointestinal tract is manufactured as follows: first, 350 mg of discrete, sodium chloride osmagent particles are coated in an air suspension machine with a film forming composition comprising (1) 70% cellulose acetate having an acetyl content of 32% mixed with (2) 30% polyethylene glycol having a molecular weight of 400 dissolved in (3) methylene chloride-methanol, 80:20, until each particle is encapsulated with the film to form the delivery member. Next, 235 mg of agent procainamide hydrochloride having a molecular weight of 271.79 is mixed with the delivery member and 100 mg of polyvinylpyrrolidone, compressed and coated in an air suspension with a wall of semipermeable polymeric cellulose acetate having an acetyl content of 32%. The cellulose acetate is intimately applied from a 5% w/w solution in acetone:water in the proportion of 89:11 wt:wt. Finally, an osmotic passageway is drilled through the wall and it had a diameter of 7.5 mils to yield the osmotic system.

EXAMPLE 6

Figure 6:
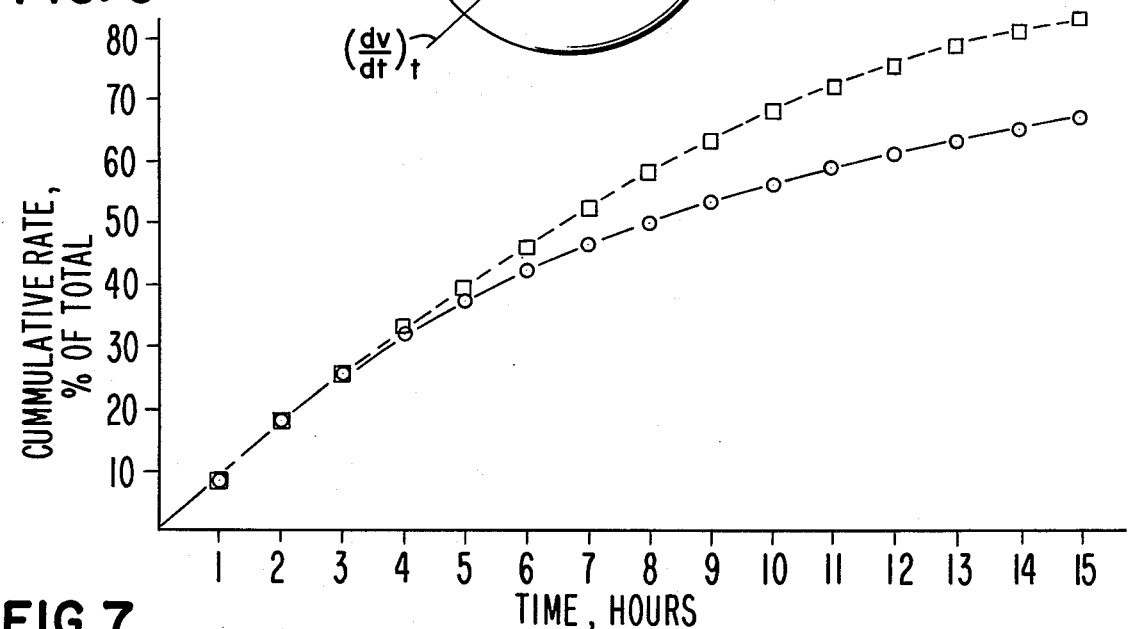
FIGS. 6, 7 and 8 are graphs recording the cummulative release, the rate of release for osmotic systems made with and without the delivery combination, and the improvement in the percent of agent delivered over time.
Figure 7:
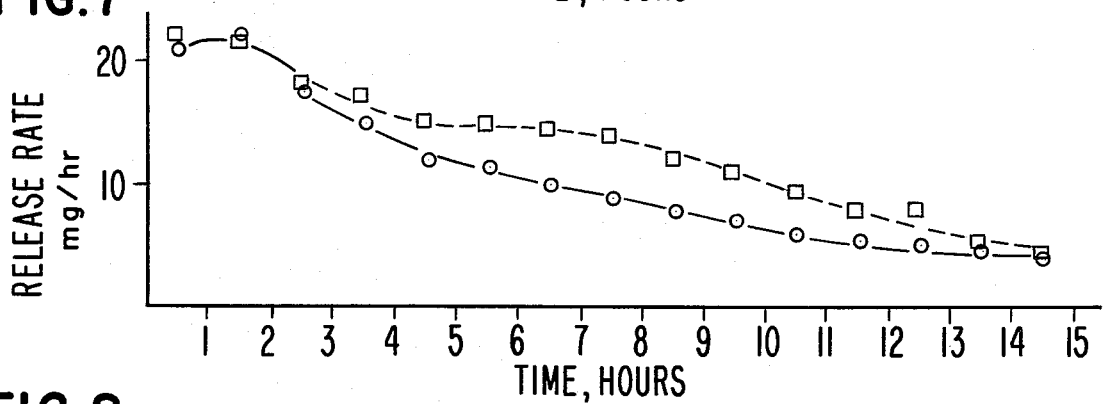
Figure 8:
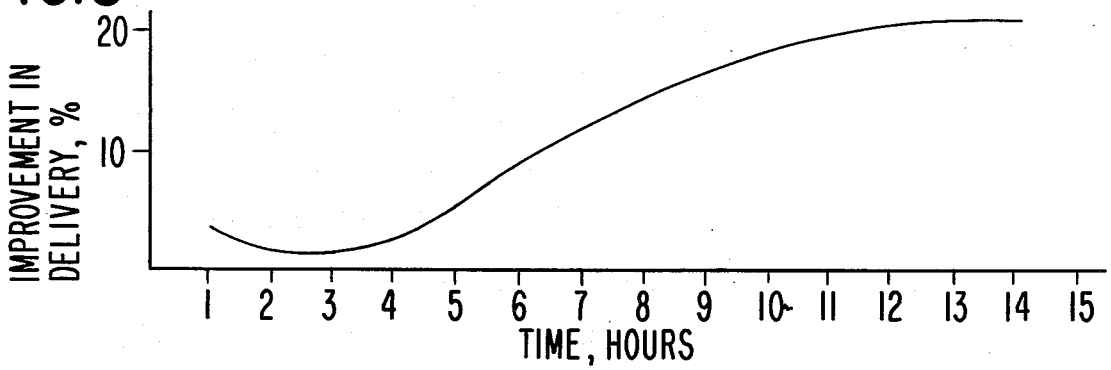

The procedure of Example 5 is repeated in this example, with all conditions as described, except that the osmotic system is manufactured with the compartment containing only 235 mg of the agent procainamide hydrochloride. The cumulative rate released expressed as percent of the total is plotted in FIG. 6 and identified by the curves with the circles. Also in FIG. 6 the release rate is plotted for a system having in its compartment 235 mg of procainamide hydrochloride, 100 mg of polyvinylpyrrolidone, and 350 mg of osmagent sodium chloride coated with a film of cellulose acetate. The release for this system is identified by the curve with the squares. In FIG. 7 the release rate in mg/hr is plotted against time for two systems. The line with the circles represents an osmotic system that contains 235 mg of procainamide hydrochloride, and the line with the squares represents a system containing in the compartment 235 mg of procainamide hydrochloride, 100 mg of polyvinylpyrrolidone, and 350 mg of osmagent sodium chloride surrounded with a semipermeable film of cellulose acetate. FIG. 8 illustrates improvement attributed to a component.

EXAMPLE 7

The procedures of Examples 5 and 6 are repeated in this example with all conditions as previously described except that the agent in compartment 13 is replaced with a member selected from the group consisting of hypnotics, sedatives, psychic energizers, tranquilizers, anticonvulsants, muscle relaxants, antiparkinson agents, analgesics, anti-inflammatory, anesthetics, muscle contractants, anti-microbials, anti-malarials, hormones, sympathomimetics, diuretics, hypolyglycemics, and nutritional agents, and the member in the compartment comprises an osmagent selected from the group consisting of sodium fluoride, ammonium chloride, a mixture of sodium chloride and ammonium chloride with the osmagent surrounded with a semipermeable film of cellulose acetate containing the film expansion agent polyethylene glycol.

EXAMPLE 8

The procedures of Examples 5, 6 and 7 are repeated in this example, with all conditions as described except that the drug in compartment 13 is replaced with a member selected from the group consisting of prochlorperazine edisylate, ferrous sulfate, aminocaproic acid, potassium chloride, mecamylamine hydrochloride, amphetamine sulphate, benzphetamine hydrochloride, isoproternol sulfate, methamphetamine hydrochloride, phenmetrazine hydrochloride, bethanechol chloride, methacholine chloride, atropine sulfate, methscopolamine bromide, isopropamide iodide, tridihexethyl chloride, phenformin hydrochloride, and methylphenidate hydrochloride, and the osmagent in the member is selected from the group consisting of potassium sulfate, sodium sulfite, potassium chloride and a mixture of potassium chloride and sodium chloride.

EXAMPLE 9

The procedures of Examples 5 and 6 are repeated in this example with all conditions as previously described except that the system is designed as an ocular, osmotic therapeutic system and compartment 13 contains an ophthalmic drug that is a member selected from the group consisting of idoxuridine, phenylephrine, pilocarpine hydrochloride, eserine, carbachol, phospholine iodine, demecarium bromide, cyclopentolate, homatropine, scopolamine and epinephrine.

EXAMPLE 10

An osmotic system designed for delivering an agent having limited solubility is designed by governing the flux of fluid into the delivery member 17 as the osmotic pressure $\pi_0$ across the composite structure of the film of the member and the wall of the osmotic system. The increase in size of the member and the rate of agent delivery from the system is housing a suspending agent with the agent having an effective particle size of 5 microns, is given by Relation 34:

$$\frac{dv}{dt} = \pi_0 \frac{1}{\frac{h_0}{A_0 k_0} + \frac{h_1}{A_1 k_1}} \tag{34}$$

wherein $h$, $k$, and $A$, with subscripts (0) and subscripts (1) and (0) have the meanings set forth above. From Relation 34 it is obvious a controlled and constant rate of release is obtained from the system when Relations 35 and 36 hold as follows:

$$\frac{h_0}{A_0 k_0} << \frac{h_1}{A_1 k_1} \tag{35}$$

$$\frac{A_0 k_o}{h_0} >> \frac{A_1 k_1}{h_1} \tag{36}$$

with controlled delivery obtained for the system as $A_1$, $k_1$, and $h_1$ are constant throughout the lifetime of the system. Hence, following Relations 34, 35 and 36, and by manufacturing systems according to the procedure set forth in Examples 5 and 6 drugs having limited solubility that can be delivered by the systems are a member selected from the group consisting of diphenidol, meclizine hydrochloride, prochloroperazine maleate, thiethylperazine maleate, anisindione, ethinyl estradiol, progesterone, diphenadione, erythrityl tetranitrate, digoxin, isoflurophate, reserpine, acetazolamide, thazolamide, bendroflumethrazide, allopurinol and aspirin. The drugs delivered by the osmotic system manufactured according to the example are in one embodiment present in the compartment in a formulation consisting of 20% drug, 49% sorbitol, 30% gelatin, and 1% magnesium stearate.

EXAMPLE 11

An osmotic delivery system manufactured in the form of an osmotic device is made as follows: first, a delivery member 17 shaped like a tablet and weighing 205 mg comprising a combination of 98% sorbitol, 2% magnesium and a trace of yellow dye is pressed in a conventional Manesty press and then coated with a film forming composition consisting of 70% cellulose acetate having an acetyl content of 32% and 30% polyethylene glycol having a molecular weight of 400. The member had a diameter of 5/16 inch, an area of 1.52 cm$^2$, the semipermeable film had a thickness of 4.0 mils and a volume of 0.137 cm$^2$. Next, 230 mg of a composition comprising 210 mg of procainamide hydrochloride, 11 mg of poly(vinyl pyrrolidone), 5 mg of carboxymethylcellulose, and 4 mg of magnesium stearate are tableted around the member 17 until the tableted mass had a diameter of 7/16 inch, a thickness of 4.82 mm, a final volume of 0.355 cm² with the procainamide hydrochloride having a volume of 0.218 cm³. Next, the procainamide hydrochloride compartment is coated with a 2.0 mil thick wall of a wall forming composition consisting of 90% cellulose acetate having an acetyl content of 38.3% and 10% polyethylene glycol having a molecular weight of 400. Finally, a passageway having a diameter of 10 mils is drilled through the wall to yield the osmotic delivery system.

The novel osmotic systems of this invention use a means for the obtainment of precise release rates in the environment of use while simultaneously maintaining the integrity and character of the system. While there has been described and pointed out features of the invention as applied to presently preferred embodiments, those skilled in the art will appreciate that various modifications, changes, additions and omissions in the systems illustrated and described can be made without departing from the spirit of the invention.

I claim:

1. An osmotic system for the controlled delivery of a beneficial agent to an environment of use, said system comprising:
   a. a wall formed of a material permeable to the passage of an external fluid in the environment of use and substantially impermeable to the passage of agent; said wall surrounding and forming;
   b. a compartment containing a beneficial agent and a suspending agent;
   c. a delivery member in the compartment comprising a film formed of an expandable semipermeable material surrounding an osmotically effective compound which compound exhibits an osmotic pressure against gradient across the film against fluid in the compartment;
   d. a passageway in the wall communicating with the compartment and the exterior of the system for delivering beneficial agent from the system; and
   e. wherein in operation, when the system is in the environment of use, fluid from the environment is imbibed through the wall into the compartment in a tendency towards osmotic equilibrium at a rate determined by the permeability of the wall and the osmotic pressure gradient across the wall, forming a suspension containing beneficial agent and activating the delivery member to imbibe fluid from within the compartment and increase in volume through sequential changes to an state, whereby through the cooperation of the suspending agent and the delivery member beneficial agent is delivered through the passageway from the system at a controlled rate over a prolonged period of time to the environment.

2. The osmotic system for delivering a beneficial agent according to claim 1 wherein said beneficial agent has limited solubility in the fluid.

3. The osmotic system for delivering a beneficial agent according to claim 1 wherein said beneficial agent is practically insoluble in the fluid.

4. The osmotic system for delivering a beneficial agent according to claim 1 wherein said beneficial agent is soluble to very soluble in the fluid.

5. The osmotic system for delivering a beneficial agent according to claim 1 wherein the compartment contains an osmotically effective compound that exhibits an osmotic pressure gradient across the wall.

6. The osmotic system for delivering a beneficial agent according to claim 1 wherein the film is formed of a semipermeable material selected from the group consisting of cellulose acetate, cellulose diacetate, cellulose triacetate, polyamide, polyurethane, and polystyrene.

7. The osmotic system for the controlled delivery of a beneficial agent according to claim 1 wherein the film contains 0.01 to 40% by weight of a film expansion agent that imparts flexibility and expandability to the film.

8. The osmotic system for the controlled delivery of a beneficial agent according to claim 1 wherein the film contains a film expansion agent selected from the group consisting of poly $(\alpha,\omega)$ alkylenediols, polyester alkylene glycol and polyalkylene glycol.

9. The osmotic system for the controlled delivery of a beneficial agent according to claim 1 wherein said beneficial agent is a particle and has a size of 0.01 to 300 microns.

10. The osmotic system for the controlled delivery of a beneficial agent according to claim 1 wherein said beneficial agent is a particle and the passageway has a diameter that permits passage of the particle.

11. The osmotic system for the controlled delivery of a beneficial agent according to claim 1 wherein the suspending agent is a member selected from the group consisting of gelatin, pectin, carboxymethylcellulose, polyvinyl pyrrolidone, polyalkylene glycols, starches and other pharmaceutically acceptable hydrophilic water soluble compounds.

12. The osmotic system according to claim 1 wherein the system is sized, shaped and adapted as a dosage form for administering a beneficial agent to the environment of use consisting of the gastrointestinal tract.

13. The osmotic system for the controlled delivery of a beneficial agent according to claim 1 wherein the beneficial agent and the suspending agent are present as a suspension and wherein imbibition of fluid by the delivery member is accompanied by an expansion in volume of the member to continuously fill the compartment and urge the suspension through the passageway.

14. The osmotic system for the controlled delivery of a beneficial agent according to claim 1 wherein the beneficial agent is slightly soluble in the external fluid.

15. The osmotic system for the controlled delivery of a beneficial agent according to claim 1 wherein the compartment contains a multiplicity of delivery members.

16. The osmotic system for delivering a beneficial agent according to claim 1 wherein the agent is a drug selected from the group consisting of central nervous system, hypnotic, sedative, antidepressant, tranquilizer, anticonvulsant, anti-parkinson, analgesic, anti-inflammatory, anesthetic, anti-infective, hormonal, sympathomimetic, diuretic, hypoglycemic, cardiac, and ophthalmic drug.

17. The osmotic system for delivering a beneficial agent according to claim 1 wherein the rate of imbibition by the delivery member is determined by the permeability of the film and the osmotic pressure gradient across the film against fluid in the compartment, and the rate of increase of the delivery member corresponds to the rate of fluid imbibition by the delivery member.

18. The osmotic system for the controlled delivery of a beneficial agent according to claim 1 wherein the delivery member in the compartment is distant from the passageway, expands and continuously fills the compartment for delivering the maximum amount of beneficial agent through the passageway from the compartment, and the suspending agent is a member selected from the group consisting of hydrophilic liquid and hydrophilic solid suspending agents.

19. A method for continuously administering a beneficial agent at a controlled rate to a biological environment comprising:
   A. admitting into the environment an osmotic system comprising:
      1. a wall formed of a semipermeable material that is permeable to the passage of fluid in the environment and substantially impermeable to beneficial agent, the wall surrounding and forming;
      2. a compartment containing the beneficial agent, a suspending agent and a delivery member, said member comprising an expandable film surrounding an osmotic agent which osmotic agent exhibits an osmotic pressure gradient across the film against fluid in the compartment;
      3. a passageway in the wall for releasing beneficial agent from the system;
   B. imbibing fluid from the environment into the compartment at a rate determined by the permeability of the wall and the osmotic pressure gradient across the wall to form a suspension containing beneficial agent and for activating the delivery member to imbibe fluid from within the compartment, increase in volume and continuously fill the compartment; and
   C. delivering the suspension containing beneficial agent from the system by said delivery member acting in cooperation with the suspending agent thereby urging the suspension through the passageway at a controlled rate which corresponds to the rate of increase in volume of the delivery member and the rate of formation of the suspension over a prolonged period of time.

20. The method for continuously delivering a beneficial agent according to claim 19 wherein the biological environment is a warm blooded animal.

21. The method for continuously delivering a beneficial agent according to claim 19 wherein said beneficial agent is a member selected from the group consisting of corticosteroids, androgens, estrogens, progestational agents, and mixtures thereof.

* * * * *